(12) United States Patent
Kelly et al.

(10) Patent No.: US 7,316,648 B2
(45) Date of Patent: Jan. 8, 2008

(54) PORTABLE PATIENT MONITORING SYSTEM INCLUDING LOCATION IDENTIFICATION CAPABILITY

(75) Inventors: Clifford Mark Kelly, Windham, NH (US); Tomas Russ, Carlisle, MA (US); Matthew Mozur, Danvers, MA (US)

(73) Assignee: Draegers Medical Systems Inc, Andover, MA (US)

( * ) Notice: Subject to any disclaimer, the term of this patent is extended or adjusted under 35 U.S.C. 154(b) by 116 days.

(21) Appl. No.: 10/864,224

(22) Filed: Jun. 9, 2004

(65) Prior Publication Data

US 2005/0033124 A1 Feb. 10, 2005

Related U.S. Application Data

(60) Provisional application No. 60/477,612, filed on Jun. 11, 2003.

(51) Int. Cl.
*A61B 5/00* (2006.01)
(52) U.S. Cl. .............. 600/300; 600/301; 128/903; 340/10.42
(58) Field of Classification Search ........ 600/300–301; 128/903–905; 340/10.42
See application file for complete search history.

(56) References Cited

U.S. PATENT DOCUMENTS

| | | | |
|---|---|---|---|
| 5,375,604 A * | 12/1994 | Kelly et al. ............. | 600/484 |
| 5,687,734 A | 11/1997 | Dempsey et al. ........ | 128/696 |
| 5,918,331 A | 7/1999 | Hall et al. .............. | 5/626 |
| 5,931,791 A | 8/1999 | Saltzstein et al. ....... | 600/513 |
| 5,936,539 A * | 8/1999 | Fuchs .................... | 128/903 |
| 6,112,502 A | 9/2000 | Frederick et al. ....... | 53/411 |
| 6,221,012 B1 | 4/2001 | Maschke et al. ........ | 600/301 |
| 6,579,231 B1 | 6/2003 | Phipps .................. | 600/300 |
| 6,681,003 B2 | 1/2004 | Linder et al. ......... | 379/106.02 |
| 2002/0032787 A1 | 3/2002 | Overton et al. ......... | 709/230 |
| 2002/0069885 A1 | 6/2002 | Boies et al. ............ | 128/99 |
| 2002/0084698 A1 | 7/2002 | Kelly et al. ............. | 307/104 |
| 2002/0109595 A1 | 8/2002 | Cairo et al. ........... | 340/573.1 |
| 2002/0145534 A1 | 10/2002 | Dempsey ............. | 340/825.49 |
| 2003/0174049 A1 * | 9/2003 | Beigel et al. ........... | 340/10.42 |
| 2003/0216625 A1 | 11/2003 | Phipps .................. | 600/300 |
| 2004/0004460 A1 | 1/2004 | Fitch et al. ............ | 320/108 |
| 2004/0064693 A1 | 4/2004 | Pabla et al. ........... | 713/168 |
| 2004/0088345 A1 | 5/2004 | Zellner et al. ......... | 709/200 |

FOREIGN PATENT DOCUMENTS

| | | | |
|---|---|---|---|
| WO | WO 0207816 | 1/2002 | ............ 1/39 |
| WO | WO 03013177 | 2/2003 | ............ 7/38 |

* cited by examiner

*Primary Examiner*—Max R Hindenburg
*Assistant Examiner*—Sharick Naqi
(74) *Attorney, Agent, or Firm*—Jack Schwartz & Associates, PLLC

(57) ABSTRACT

A docking station advantageously provides a location identifier to a portable processing device which processes the location identifier to determine docking station location (and other information) and to upload settings and configuration information related to an identified location which is retained until a different docking station location is encountered. In a system for use in a docking station suitable for attaching to a portable patient monitoring device for processing signal parameters acquired from a patient, a power coupler couples power to provide electrical power to a portable processing device. An adaptive communication interface, in a first mode of operation, communicates an identifier associated with a particular docking station to the portable processing device, and in a second mode of operation, establishes connection of the portable processing device to a network.

30 Claims, 2 Drawing Sheets

# PORTABLE PATIENT MONITORING SYSTEM INCLUDING LOCATION IDENTIFICATION CAPABILITY

This is a non-provisional application of provisional application Ser. No. 60/477,612 by C. Kelly et al. filed 11 Jun. 2003.

FIELD OF THE INVENTION

The present invention relates to a portable patient monitoring device and associated docking station supporting location identification.

BACKGROUND OF THE INVENTION

Present day monitoring devices are typically designed specifically for different care areas inside or outside of a hospital. In the case of a trauma patient, the monitoring typically begins at the site of the accident. Ambulances carry transport monitors, which have been designed to be rugged for use in mobile ground and air vehicles. The patient is transported to the hospital and may initially be held in an emergency room (ER) for evaluation of the severity of the accident or illness. This usually requires disconnecting the patient from the ambulance monitor and reconnecting the patient to the ER monitor. Monitors for this area of the hospital often have a wireless connection to a central station monitor and information network allowing the monitor and patient to be mobile so they can be deployed, viewed, and controlled where needed in the ER. If a patient is critically ill the patient is typically taken to an operating room (OR) or to an Intensive Care Unit (ICU), and again disconnected from the ER monitor and reconnected to the OR or ICU monitor.

A patient is usually moved from an OR to a recovery area and then to an ICU, or from an ICU to a less-acute "step-down" area or "ward", and again may need to be physically disconnected and reconnected from the OR monitor to a transport monitor or to an ICU or step-down monitor. Healthier patients may be outfitted with wearable "Telemetry" devices that are semi-mobile or mobile to allow a patient to leave the bedside and ambulate within a care unit or hospital. Fully ambulatory patients may be permitted exercise by walking within a specific area designated by a clinician. After further improvement in physiological status a patient may be no longer need to be continuously monitored but has vital signs periodically spot-checked and is eventually given a final complete evaluation before discharge.

It is desirable that a portable patient monitoring device with fixed and mobile modes of operation is used to support the different patient treatment stages in order to continuously monitor a patient even during those times when a patient is in transit, e.g., between patient room, examining room, operating room, etc. It is further desirable that a portable patient monitoring device is able to identify patient location or at least a location of a current docking station to which it is attached in a fixed mode of operation. Known systems used to determine location information of a portable device attached to a docking station use complex docking station technology and are consequently costly, lower in reliability and are typically also power hungry. These factors are particularly burdensome when large quantities of docking stations are employed in a hospital, for example. A system according to invention principles addresses this problem and associated problems.

SUMMARY OF INVENTION

A docking station advantageously provides a location identifier to a portable processing device which processes the location identifier to determine docking station location (and other information) and to upload settings and configuration information related to an identified location which is retained until a different docking station location is encountered. In a system for use in a docking station suitable for attaching to a portable patient monitoring device for processing signal parameters acquired from a patient, a power coupler couples power to provide electrical power to a portable processing device. An adaptive communication interface, in a first mode of operation, communicates an identifier associated with a particular docking station to the portable processing device, and in a second mode of operation, establishes connection of the portable processing device to a network.

DETAILED DESCRIPTION OF INVENTION

A docking station advantageously stores a code (a location identifier) and provides the location identifier to a portable processing device docked with the docking station (or in the vicinity of the docking station in a wireless communication embodiment). The portable processing device comprises a portable medical device such as a patient parameter monitoring device but may also be another portable device such as an infusion pump, a PDA (Personal Data Assistant) for use by a physician, ventilation apparatus, anesthesiology apparatus or another portable medical device. The portable processing device determines docking station location (and other information) using the location identifier received from the docking station. This system uses processing resources in a portable processing device and enables a simple, cost effective docking station to be employed. Substantial cost reduction and simplification improvement is derived since there are typically many more docking stations than portable devices in a system and the portable processing devices usually contain surplus processing resources. The portable device location determination functions advantageously use processing functions already present in the portable processing device. This minimizes any added complexity and cost to the portable device. The system acquires a unique location identifier code from the docking station and uses it to identify the docking station location and stores this information to identify the portable device last fixed location when in a mobile mode of operation. This information is used to identify the last location of a patient when the device was last docked and is used to upload settings related to the location which are retained until the portable device detects a different docking station location.

Figure 1:
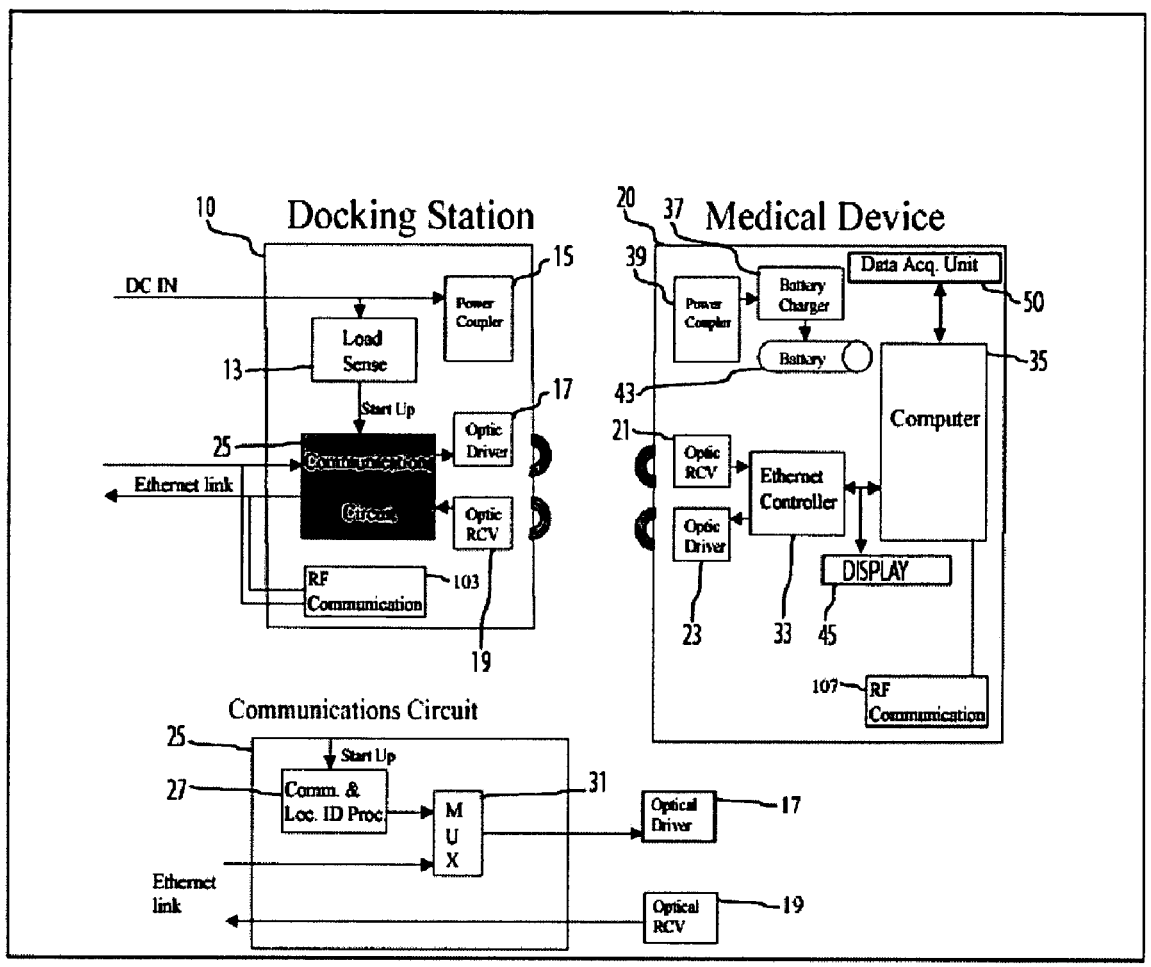
FIG. 1 is a block diagram of a system including a docking station and portable processing device, according to the principles of the invention.

FIG. 1 is a block diagram of a system including docking station 10 and portable processing device 20. Docking station 10 and portable processing device 20 use inductive coupling for power coupling and use optical transmission for inter-device communication. Docking Station 10 maintains a location identifier code used for identifying a geographical location (i.e., a position in a hospital comprising a care unit, floor, wing, street address, for example). The location identifier is associated with a particular docking station and comprises an Ethernet compatible MAC address, an IP address, a port identifier, an Internet compatible address, a LAN address or another electronic code that is associated in a stored map with a geographic location. The map may be stored in portable device 20 or in a remote repository on a network. Multiple portable patient monitors are monitored by a central monitoring system typically supervised by a nurse. Docking station 10 provides several functions for portable medical devices such as device 20. Docking station 10 provides a physical mount for a portable device and recharges portable device batteries and provides power directly to a portable device. Docking station 10 also establishes communication connections between portable device 20 and networks and other devices. For this purpose, in the exemplary embodiment, portable device 20 establishes Ethernet protocol compatible communication via docking station 10 to a hospital Local Area Network (LAN), for example. In other embodiments different communication protocols may be used. The Ethernet communication protocol standard is used to establish communication to different diagnostic medical devices in a hospital and is capable of supporting communication with many devices internal and external to a hospital, for example. Further, an identifier is attached to data packets conveyed using Ethernet communication and comprises a number called an Ethernet (or MAC) Address, which uniquely identifies devices on an Ethernet network. However, in Ethernet compatible network communication, the physical network is divorced from conveyed data. Consequently, the source of a received Ethernet message is known but not the physical location of a transmitting device sending the message.

Docking station 10 employs communication interface 25 for establishing and maintaining Ethernet compatible communication via a hospital LAN, for example. In a healthcare setting such as a hospital it is desirable to be able to determine the location of portable medical (e.g., patient monitoring) device 20 and the docking station 10 to which it is attached in order to report the location of a patient (e.g., via a hospital LAN to an executable management application), as well as to provide other functions. A docking station is fixed in location and a portable medical device is freely movable. Docking station 10 stores physical location information in the form of a location identifier (such as an Ethernet MAC address) for transmission to requesting portable processing device 20. Docking station 10 employs communication interface 25 to manage a communication link with a docked portable processing device (e.g., device 20) to facilitate identification of the location of docking station 10 by the portable device.

Docking station 10 communicates a location identifier via interface 25 and optical transmission drivers 17 to optical receiver 21 and adaptive communication interface (Ethernet communication controller) 33 of docked portable device 20. In response to docking of portable device 20 in docking station 10, power coupler 15 operating from a voltage supply couples electrical power via coupler 39 to device 20. Power coupler 15 and coupler 39 may comprise a known transformer arrangement for electrically isolated coupling of electrical power, for example. Coupler 39 charges batteries 43 via charging unit 37 and provides power to an internal power supply to provide power to operate the portable patient monitor. Batteries 43 provide electrical power for portable device 20 in its mobile undocked mode of operation. Controller 35 controls operation of device 20 based on stored pre-programmed instruction and directs processing of patient parameter data for presentation on display 45. Portable device 20 includes a data acquisition processor 50 for receiving patient parameter data from multiple different patient attached sensors. This received patient parameter data is processed by acquisition processor 50, operating in conjunction with controller 35, to provide processed patient parameter data for presentation on display 45. The processed patient parameter data comprises physiological data including, electrocardiograph (ECG) data, blood parameter data, ventilation parameter data, infusion pump related data, blood pressure data, pulse rate data and temperature data. Controller 35 manages electrically isolated bidirectional Ethernet compatible communication with docking station 10 using Ethernet controller 33. Ethernet compatible data is bidirectionally communicated between Ethernet controller 33 and a hospital LAN via docking station 10 using electrically isolated driver 23 receiver 19 as well as electrically isolated receiver 21 and driver 17.

Upon initial docking, load sense unit 13 detects power is being supplied by docking station 10 to device 20 and provides a signal, indicating device 20 is docked with docking station 10, to communication control unit 27 in communication interface 25. In response to this initial docking sense signal and to a determination that there is an active Ethernet communication link between docking station 10 and device 20, unit 27 directs multiplexer 31 to interrupt the Ethernet compatible communication link between portable device 20 and the hospital LAN. This enables unit 27 to provide a message in a first mode of operation via multiplexer 31 to portable device 20 via the Ethernet communication link optical driver 17 and receiver 21 in response to the initial docking sense signal and active Ethernet link determination. A message is sent each time portable device 20 is docked with a docking station. The message includes an identifier (e.g., MAC address) associated with docking station 10 that enables portable device 20 (or a remote device) to determine a geographic location of docking station 10 from a map associating docking station identifiers with corresponding geographic locations of the docking stations. If portable device 20 is not powered on when it is docked, or if device is turned off 20 while docked, the message is not sent until the device is powered on.

In response to sending the message communication interface 25, in a second mode of operation, establishes connection of portable processing device 20 with the hospital LAN. Portable patient monitoring device 20 communicates the identifier associated with docking station 10 to a remote device via the hospital LAN in the second mode of operation. Device 20 communicates a location related identifier derived (using the map) based on the particular docking station identifier or an identifier identifying portable processing device 20 to the remote device. Specifically, adaptive communication interface 33 of device 20 communicates the identifier associated with docking station 10 or a location related identifier derived based on the docking station identifier, to the remote device. This is communicated by wireless or wired communication. Adaptive communication interface 33 in conjunction with controller 35 adaptively switches between a wireless network connection when undocked and a docking station supported wired network connection when docked in docking station 10.

In response to communication of the docking station 10 identifier to the remote device, portable patient monitoring device 20 receives from the remote device via the hospital LAN and docking station 10 one or more information items. The information items include, patient geographic location information derived based on the docking station 10 identifier, configuration information for use in configuring portable patient monitoring device 20 based on geographic location, configuration information for use in selecting particular features of the portable patient monitoring device 20 for activation based on geographic location and information supporting operation of device 20 with a second device associated with the geographic location. Additional information items include an alarm setting associated with a patient parameter and configuration information for use in selecting particular features of portable device 20 for activation based on geographic location and user entitlement information. In another embodiment, one or more of the information items may be derived directly by portable device 20 based on the received identifier associated with docking station 10.

The described information items are usable for, determination of patient location, configuring device 20 to suit a particular location, configuring particular secured features of device 20 based on location and for associating device 20 with other devices in a room or attached to a patient, for example. Multiple portable patient monitoring devices used by a single particular patient are associated with a particular patient by docking the multiple portable patient monitoring devices into a single particular docking station, for example,. Portable processing device 20 also employs a unique identifier (a MAC address or another identifier) different to the docking station 10 identifier. The portable device 20 identifier in another embodiment may be used in conjunction with the docking station identifier for use in providing information to a central monitoring system (monitoring multiple docking stations) or for acquiring particular information items as previously described for use by a particular device 20 in a particular location.

A central monitoring system monitors multiple portable devices of a group of patients and communicates with a portable device (such as device 20) via docking stations (such as docking station 10), for example. The central monitoring system processes alarm signals and other data from the portable devices. In response to receiving an alarm from portable device 20 via station 10, a central monitoring system uses a received docking station identifier (and in another embodiment also a device 20 identifier) to indicate a location of device 20 (and docking station 10). The central monitoring system responds to a received alarm by identifying a location by generating a text message, initiating activation of an alarm indicator (e.g., by activating an alarm light adjacent a patient room) or by initiating display of an alarm and associated location on a reproduction device, (e.g. by a displayed icon on a map).

Further, a user enters configuration settings (e.g., alarm settings) that vary based on portable processing device 20 location using the central monitoring system. The entered settings are communicated via the hospital LAN to device 20 for use in patient parameter monitoring functions. Similarly, a user enters data or commands using a central monitoring system (or other processing device on the hospital LAN) to enable particular functions based on location of portable monitoring device 20 and based on predetermined payment, entitlement or license criteria. User entered data and configuration settings received by portable device 20 are stored by controller 35 in internal memory. The stored data may include, for example, an identifier (and other information) associated with a previous docking station (or received via the previously used docking station) prior to the subsequent docking station and employed by portable device 20. The stored data may also include, information derived using an identifier associated with the previously used docking station and a time and date stamp of undocking. The user entered data and configuration settings related to a last docked location remain in effect until they are manually changed or are changed by virtue of portable device 20 detecting a new docking at a different docking station location. The central monitoring system (and any other device on the hospital LAN) communicates with portable processing device 20 via the LAN and docking station 10 interface unit 25 whilst device 20 is docked. The central monitoring system and other LAN devices also communicate wirelessly with device 20 when it is undocked and in a mobile mode of operation via wireless communication implemented by RF communication unit 107. Unit 107 includes multiple wireless communication transceivers (individually including a receiver and transmitter pair) using wireless technologies which may include at least one of, Wireless Local Area Network (WLAN), e.g., 802.11a, 802.11b, 802.11g standard compatible communication, Wireless Patient Area Network (WPAN), e.g., 802.11a, 802.11b, 802.11g, 802.15.x standard compatible communication, or Wireless Wide Area Network (WWAN) e.g. GSM/GPRS standard compatible communication, for example. RF communication unit 107 supports communication with a wireless locator engine for continuously tracking location of a patient throughout a hospital, for example.

In another embodiment docking station 10 similarly supports wireless communication with LAN devices or portable device 20 implemented by RF communication unit 103. Unit 103 includes multiple wireless communication transceivers (individually including a receiver and transmitter pair) using one or more wireless technologies including WLAN 802.11a, 802.11b, 802.11g, 802.15.x, WPAN, and GSM/GPRS. The portable monitor device 20 supports the above mentioned wireless communications functions using communication interfaces installed by a plugin card, for example.

Controller 35 of portable patient monitoring device 20 uses the elapsed time duration occurring since last docking with a docking station together with location information derived using the identifier associated with the last docking station in order to estimate a current location of device 20. For this purpose, controller 35 uses a likelihood estimation. The likelihood estimation is based on the assumption that the shorter the elapsed time duration since the last docking, the more likely it is a current undocked location is likely to be near the last docked location.

Figure 2:
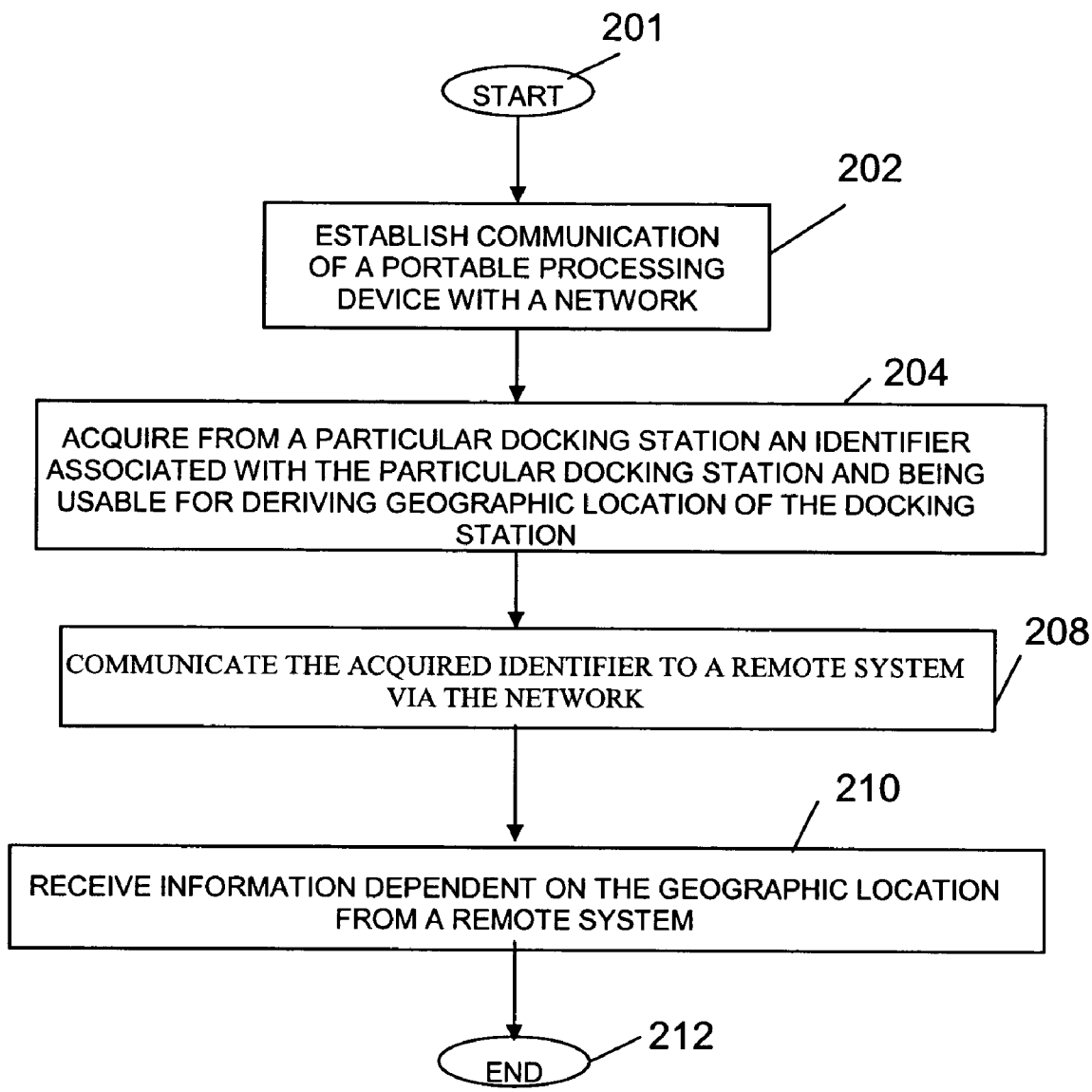
FIG. 2 shows a flowchart of a method for processing docking station location information, according to the principles of the present invention.

FIG. 2 shows a flowchart of a method for processing docking station location information performed by controller 35 of portable device 20. In step 202 following the start at step 201, controller 35 directs communication interface 33 in establishing bidirectional communication of device 20 with a hospital LAN. In step 204 controller 35 directs communication interface 33 in acquiring from docking station 10 an identifier that is associated with this docking station and is usable for deriving geographic location of docking station 10. Controller 35 in conjunction with interface 33 in step 208 communicates the acquired identifier to a remote system via the hospital LAN. In response in step 210 interface 33 receives information from the remote system dependent on the geographic location of docking station 10. The process of FIG. 2 terminates at step 212.

The difficulties involved in making power and communication connections between a docking station and a portable processing device increase in importance as new generations of devices shrink in size. Therefore, for reasons of cost and size, it is advantageous to achieve the features of the location identification processing system without adding a separate communication channel and to use an existing docking station to portable device communication link. In another embodiment a second channel is used to support the location and other information determination system. Further, the system is usable in any device that has both a portable and fixed mode of operation.

The System and process presented in FIGS. 1 and 2 are not exclusive. Other systems and processes may be derived in accordance with the principles of the invention to accomplish the same objectives. Although this invention has been described with reference to particular embodiments, it is to be understood that the embodiments and variations shown and described herein are for illustration only and that various modifications may be implemented by those skilled in the art without departing from the scope of the invention. A location processing system according to invention principles may be used for monitoring location in any system involved mobile devices with fixed communication points and may be used with a wireless locator engine to support continuous tracking of location of a patient throughout a hospital, for example.

What is claimed is:

1. A system for use in a docking station suitable for attaching to a portable patient monitoring device, said portable patient monitoring device being for processing signal parameters acquired from a patient, comprising:
    a power coupler coupling power to provide electrical power to a portable processing device; and
    a controller determining whether said portable processing device is attached to a particular docking station and is powered on;
    a communication interface,
        in a first mode of operation, communicating a location identifier associated with said particular docking station to said portable processing device, and
        in a second mode of operation, establishing connection of said portable processing device to a network enabling determination of a geographic location of said particular docking station using said location identifier, transmitting of configuration settings related to the determined geographic location to said particular docking station and transmitting patient data to said network, said first mode of operation being inhibited until said determination is made by said controller preventing changing of configuration settings until said controller determines said portable processing device is attached to said particular docking station and is powered on.

2. A system according to claim 1 wherein
said controller initiates said first mode of operation and subsequently initiates said second mode of operation.

3. A system according to claim 2 wherein
said controller detects said portable processing device is attached to said particular docking station by detecting at least one of, (a) an active communication link to said network is present, (b) an active communication link is present between said particular docking station and said portable processing device and (c) a portable patient monitoring device is docked with said particular docking station and receiving electrical power from said particular docking station.

4. A system according to claim 3 wherein
in response to said detection, said controller initiates interruption of said active communication link and communicates said location identifier associated with said particular docking station to said portable processing device in said first mode of operation and subsequently re-connects said active communication link to said network in said second mode of operation.

5. A system according to claim 3 wherein
said active communication link comprises an Ethernet compatible communication link.

6. A system according to claim 1 wherein said controller further determines a patient location by calculating a likelihood estimation derived based on a most recent communication of said location identifier and said likelihood estimation evaluates the time since said portable processing device was docked at said particular docking station having an associated location identifier and determines the location of the patient relative to said particular docking station.

7. A system according to claim 1 wherein
said adaptive communication interface supports communication using wireless technologies including at least one of, (a) WLAN 802.11b standard compatible communication, (b) 802.11a standard compatible communication, (c) 802.11g standard compatible communication, (d) 802.15 standard compatible communication, and (e) GSM/GPRS standard compatible communication.

8. A system for use in a portable patient monitoring device for monitoring and processing signal parameters acquired from a patient and being suitable for being attached to a docking station, comprising:
    a power coupler processing power received via a power coupler to provide electrical power for said portable patient monitoring device; and
    a controller determining whether said portable processing device is attached to a particular docking station and is powered on;
    an adaptive communication interface, using said electrical power,
        in a first mode of operation, receiving a location identifier associated with a particular docking station, and
        in a second mode of operation, establishing connection of said portable patient monitoring device to a network enabling determination of a geographic location of said particular docking station, transmitting of configuration settings related to the determined geographic location to the docking station and transmitting patient data to said network, said first mode of operation being inhibited and the configuration settings are prevented from being changed until said determination is made by said controller.

9. A system according to claim 8 including
a data acquisition processor receiving and processing patient parameter data from a plurality of different patient attached sensors to provide processed patient parameter data; and
an image reproduction device displaying processed patient parameter data.

10. A system according to claim 8 wherein
said adaptive communication interface communicates processed patient parameter data to a docking station when said portable patient monitoring device is attached to said particular docking station.

11. A system according to claim 10 wherein
said processed patient parameter data comprises physiological data including at least one of, (a) electrocardiograph (ECG) data, (b) blood parameter data, (c)

ventilation parameter data, (d) infusion pump related data, (e) blood pressure data, (f) pulse rate data and (g) temperature data.

12. A system according to claim 8 wherein
said power coupler comprises a power unit re-charging a battery and supplying power to said portable patient monitoring device and
said adaptive communication interface communicates said location identifier to said network via wireless communication.

13. A system according to claim 8 wherein
said controller determines said geographic location of said particular docking station from a map associating said identifier with a corresponding geographic location.

14. A system according to claim 8 wherein
said portable patient monitoring device communicates, to a remote device via said network in said second mode said particular docking station location identifier and
in response, said portable patient monitoring device acquires at least one of, (i) patient geographic location information, (ii) configuration information used in configuring said portable patient monitoring device based on geographic location, (iii) configuration information used in selecting particular features of said portable patient monitoring device for activation based on geographic location and (iv) information supporting operation of said portable patient monitoring device with a second device associated with said geographic location.

15. A system according to claim 14 wherein
said portable patient monitoring device acquires said information in response to an identifier of said portable processing device.

16. A system according to claim 8 wherein
said portable patient monitoring device communicates, to a remote device via said network in said second mode, said particular docking station location identifier and
in response, said portable patient monitoring device acquires at least one of, (i) an alarm setting associated with a patient parameter and (ii) configuration information used in selecting particular features of said portable patient monitoring device for activation based on geographic location and user entitlement information.

17. A system according to claim 8 wherein
said location identifier associated with said particular docking station comprises at least one of, (a) an Ethernet compatible MAC address, (b) an IP address, (c) a port identifier, (d) an Internet compatible address and (e) a LAN address.

18. A system according to claim 8 wherein
said location identifier associated with said particular docking station enables determination of an association of a plurality of medical devices with a particular patient.

19. A system according to claim 8 wherein
said portable patient monitoring device communicates said particular docking station location identifier to a remote device via said network in said second mode, and enabling said remote device to use said location identifier to initiate identification of a location derived based on said location identifier.

20. A remote system according to claim 19 wherein
said remote device uses said location identifier to initiate identification of said location by at least one of, (a) generating a text message, (b) initiating activation of an alarm indicator and (c) initiating display of an alarm and associated location on a reproduction device.

21. A system according to claim 8 wherein
said adaptive communication interface couples a data transducer in said portable patient monitoring device to a corresponding transducer in said particular docking station to support connection of said portable patient monitoring device to said network and to bidirectionally exchange data.

22. A system according to claim 8 wherein
said adaptive communication interface communicates said particular docking station location identifier by at least one of, (i) wireless and (ii) wired, communication.

23. A system according to claim 8 wherein
said adaptive communication interface supports communication using wireless technologies including at least one of, (a) WLAN 802.11b standard compatible communication, (b) 802.11a standard compatible communication, (c) 802.11g standard compatible communication, (d) 802.15 standard compatible communication, and (e) GSM/GPRS standard compatible communication.

24. A system according to claim 8 wherein
said adaptive communication interface adaptively switches between a wireless network connection when undocked and a docking station supported wired network connection when docked in said particular docking station.

25. A system according to claim 8 including
a memory storing at least one of, (a) a location identifier associated with a previous docking station employed by said portable patient monitoring device prior to a subsequent docking station, (b) information derived using said location identifier associated with said previous docking station and (c) a time stamp of undocking.

26. A system for use in a portable patient monitoring device for monitoring and processing signal parameters acquired from a patient and being suitable for being attached to a docking station, comprising:
a power coupler processing power received via a power coupler to provide electrical power for said portable patient monitoring device; and
a controller determining whether said portable patient monitoring device is attached to a particular docking station and is powered on;
an adaptive communication interface, using said electrical power,
establishing connection of said portable processing device to a network and
acquiring from a particular docking station a location identifier associated with said particular docking station and deriving geographic location of said particular docking station and transmitting of patient data to said network, said acquiring of a location identifier being inhibited until said determination is made by said controller,
communicating said location identifier to a remote system via said network
receiving information including configuration settings dependent on said geographic location from a remote system when said controller determines said portable patient monitoring device is attached to said particular docking station is powered on; and
preventing receipt of configuration settings until said controller determines said portable patient monitoring device is attached to said particular docking station and is powered on.

27. A system according to claim 26 wherein
said location identifier is usable by a remote system determining location of a patient attached to said portable patient monitoring device.

28. A method for use by a docking station suitable for attaching to a portable patient monitoring device, said portable patient monitoring device being for processing signal parameters acquired from a patient, comprising the activities of:
coupling power to provide electrical power to a portable processing device; and
determining, using a controller, said portable patient monitoring device is attached to a particular docking station and is powered on;
in a first mode of operation, communicating a location identifier associated with a particular docking station to said portable processing device, and
in a second mode of operation, establishing connection of said portable processing device to a network enabling determination of a geographic location of said particular docking station, transmitting configuration settings related to the determined geographic location and transmitting of patient data to said network, said first mode of operation being inhibited until said determination is made that said portable patient monitoring device is attached to said particular docking station and is powered on preventing changing of configuration settings until the controller determines said portable processing device is attached to said particular docking station and is powered on.

29. A method for use by a portable patient monitoring device for monitoring and processing signal parameters acquired from a patient and being suitable for being attached to a docking station, comprising the activities of:
processing power received via a power coupler to provide electrical power for said portable patient monitoring device; and
determining, using a controller, said portable patient monitoring device is attached to a particular docking station and is powered on;
employing said electrical power in,
receiving a location identifier associated with a particular docking station in a first mode of operation, and
establishing connection of said portable processing device to a network in a second mode of operation enabling determination of a geographic location of said particular docking station, transmitting configuration settings related to the determined geographic location and transmitting of patient data to said network, said first mode of operation being inhibited until said determination is made that said portable patient monitoring device is attached to said particular docking station and is powered on preventing changing of configuration settings until the controller determines said portable processing device is attached to said particular docking station and is powered on.

30. A method for use by a portable patient monitoring device for monitoring and processing signal parameters acquired from a patient and being suitable for being attached to a docking station, comprising the activities of:
determing, using a controller, said portable patient monitoring device is attached to a particular docking station and is powered on;
establishing communication of said portable processing device with a network
acquiring from a particular docking station a location identifier associated with said particular docking station and deriving geographic location of said particular docking station, said acquiring of said location identifier being inhibited until said determination is made that said portable processing device is attached to said particular docking station and is powered on;
communicating said location identifier to a remote system via said network;
receiving information including configuration settings dependent on said geographic location from a remote system when said controller determines said portable patient monitoring device is attached to said particular docking station is powered on; and
preventing receipt of configuration settings until said controller determines said portable patient monitoring device is attached to said particular docking station and is powered on.

* * * * *